United States Patent [19]
Lubin et al.

[11] Patent Number: 5,991,730
[45] Date of Patent: Nov. 23, 1999

[54] METHODS AND SYSTEMS FOR AUTOMATED PATIENT TRACKING AND DATA ACQUISITION

[75] Inventors: Brian A. Lubin; Hugh P. Deaner, both of Chapel Hill, N.C.

[73] Assignee: Queue Corporation, Chapel Hill, N.C.

[21] Appl. No.: 08/947,293

[22] Filed: Oct. 8, 1997

[51] Int. Cl.[6] .................................................. G06F 17/60
[52] U.S. Cl. ................................. 705/3; 395/202; 705/2; 340/825
[58] Field of Search ..................................... 364/167, 468, 364/825; 705/2, 3, 10; 395/202

[56] References Cited

U.S. PATENT DOCUMENTS

| | | |
|---|---|---|
| 3,573,441 | 4/1971 | Glazar . |
| 3,949,196 | 4/1976 | Spalti et al. . |
| 4,222,111 | 9/1980 | Sloan et al. . |
| 4,530,067 | 7/1985 | Dorr . |
| 4,583,280 | 4/1986 | Corrigan et al. . |
| 4,794,377 | 12/1988 | Benages . |
| 5,006,983 | 4/1991 | Wayne et al. . |
| 5,018,067 | 5/1991 | Mohlenbrock et al. . |
| 5,072,383 | 12/1991 | Brimm et al. . |
| 5,166,499 | 11/1992 | Holland et al. . |
| 5,245,163 | 9/1993 | Yehuda . |
| 5,291,399 | 3/1994 | Chaco et al. ................................. 705/3 |
| 5,321,396 | 6/1994 | Lamming et al. . |
| 5,328,169 | 7/1994 | Mandel . |
| 5,455,851 | 10/1995 | Chaco et al. ................................. 379/38 |
| 5,465,082 | 11/1995 | Chaco et al. ........................ 340/825.54 |
| 5,502,806 | 3/1996 | Mahoney et al. . |
| 5,522,044 | 5/1996 | Pascucci et al. . |
| 5,541,835 | 7/1996 | Dextraze et al. . |
| 5,550,359 | 8/1996 | Bennett . |
| 5,737,280 | 4/1998 | Kokubo . |
| 5,760,704 | 6/1998 | Barton et al. . |
| 5,822,544 | 10/1998 | Chaco et al. ................................. 705/2 |

OTHER PUBLICATIONS

Varitronics Inc. materials related to CS2000 no date.
Expeditor Systems brochure and home page 1996.
Client–Tel Light System brochure no date.
"The Berdy Smartcard™ and SmartClinic™ Systems", Medical Practice Management Mar./Apr., 1995.

*Primary Examiner*—James P. Trammell
*Assistant Examiner*—Yehdega Retta
*Attorney, Agent, or Firm*—Myers Bigel Sibley & Sajovec

[57] ABSTRACT

Patient flow is automatically tracked through a medical clinic and data is acquired from the automated patient flow tracking. A file is associated with a patient including a patient identification indicator when the patient enters the facility and placement of the file in a receptacle along with the identification is detected by sensors in a receptacle located of at first service location. Removal of the file from the receptacle when a first service provider commences service is further detected. Placement of the file in a second receptacle is detected upon completion of the service. One receptacle may be a physician receptacle and the other may be a nurse receptacle. A patient visit data record is generated based upon the detected movement of the file including determining treatment time and waiting time based on marking the time of events when the file is removed and replaced in respective receptacles. Indications of patient status are further provided at the receptacle location or transmitted to a remote location. Patient flow tracking is preferably provided by receptacles at various locations to follow the treatment of the patient to entry of the service provider through ancillary services and checkout.

12 Claims, 9 Drawing Sheets

METHODS AND SYSTEMS FOR AUTOMATED PATIENT TRACKING AND DATA ACQUISITION

FIELD OF THE INVENTION

The invention relates to patient tracking, and, more particularly, to patient tracking and data acquisition in a medical clinic.

BACKGROUND OF THE INVENTION

Medical service providers, such as physicians, often provide services to their patients in an office (clinic or facility) or other ambulatory treatment environment. A typical clinic visit may be considered as a sequence of related interactions between the patient and the staff of the service provider. For example, the patient may first be greeted and logged in by a receptionist. The patient may then be called by a nurse and taken from the reception area to one of a plurality of examination rooms. The nurse may perform some initial analysis of the patient and then depart. The physician will then, typically, follow the nurse's visit and perform a physician examination of the patient. A follow up visit from the nurse may then be required after which the patient, depending upon the results of the examinations, may be taken to an ancillary service provider, such as a lab technician or to another clinic in the same facility, for additional test work. Finally, the patient may be taken to an exit area where payment for the expenses of the visit and scheduling of the next visit is arranged. With the increasing size of many physician practices, large numbers of patients may be concurrently going through processing at the physician's clinic through different examination rooms with a variety of nurses, physicians and lab technicians. The patient's records are typically tracked by providing a patient specific file containing the patient's examination information, both from the current and previous visits. The file is moved along with the patient from location to location within the clinic. There also may be service provider associated locations such as the physician's clinic and/or nurse's stations within the clinic. Multiple clinics may be located in one building or campus allowing a patient to schedule interdependent visits with multiple providers.

As the scale of medical clinic operations increase, the complexity of tracking both the physical location, movement and status of patients as well as maintaining control over patient related information becomes increasingly challenging. Accordingly, a variety of approaches to tracking patient flow or movement and data acquisition have been proposed. An example of such a system is a push button system. A typical push button system involves manual push buttons at locations within the physician's clinic and indicator lights, typically put at a remote location from the examination rooms, such as a panel in a location visible to staff members to allow calling of a staff member by a doctor. Buttons are pushed by various staff members and physicians to indicate their locations and indicator lights are driven responsive to the push buttons to provide, for example, an indication to others of where a physician is located or when a staff person is needed. An example of such a system is the Expeditor System from Expeditor Systems of Alpharetta, Ga.

A variation on a push button system involves the use of keyboard entry of data by staff members to allow more detailed, patient specific information to be entered into a tracking system. Keyboard entry systems are typically offered for use in environments with highly variable flow paths for patient treatment where the added expense of maintaining keyboards for input and committing staff to data entry connected with patient tracking may be justified. A further variation on a push button system is the Client-Tel system from Client-Tel of Milford, N.J. The Client-Tel system provides a chart rack with detectors in the reception area. When a patient arrives or an urgent message is received, the chart or message is placed in the slot of the rack associated with the requested service provider based on name plate designations on each slot. An indicator light is then activated at a remote location from the rack next to the corresponding name plate of the person who is requested to check with the front desk for a message or to meet a patient.

A further variant of prior approaches are systems directed primarily to tracking clinical information as contrasted with patient flow control. Such systems have been proposed which utilize computer data processing and storage capabilities to increase the accessibility and range of patient records available to service providers such as physicians. With the advent of smart cards, variants on such systems have been proposed that utilize a patient smart card which can be maintained by the patient allowing the patient to bring with him to a service provider extensive information regarding the patient's medical records in an electronic form. An example of such a system is the Berdy Smart-Card™ from Berdy Medical Systems in Rochelle Park, N.J.

A further variant on push button patient tracking systems includes the addition of infrared tracking to locate and follow the movement of individuals, typically, physicians. Utilizing such systems, the presence of a physician carrying an infrared transmitter is detected from infrared receivers located in various locations in the medical clinic such as examination rooms. However, such systems require additional burdens on the physicians and/or patients as it requires that an additional device, which may be easily misplaced or forgotten, be maintained on the individual. If the infrared transmitter is forgotten or lost, the expensive overhead of the sensor system becomes unreliable and fails to provide the desired information. An example of such a system is the CS2000 from Varitronics, Inc.

Each of these approaches suffers from various limitations. For example, push button indicator systems, in practice, tend to be unreliable as the service providers do not consistently operate the push buttons resulting in a breakdown of the patient status logic. Push button systems also typically do not track patient specific information. In contrast, keyboard based systems which provide for patient specific tracking of flow and data acquisition suffer from the added complexity and expenses of making keyboards available for data input and utilizing additional staff member time in entering the additional information manually.

SUMMARY OF THE INVENTION

It is, therefore, an object of the present invention to provide improved and more reliable patient tracking control and communication between service providers in a medical clinic through automated tracking of patient location and status. It is a further object of the present invention to provide methods and systems which acquire and store data based on automated patient tracking which data may later be processed to provide information about services provided to the patient such as patient waiting time and examination time.

It is an additional object of the present invention to provide methods and systems of patient tracking which automatically track patients based on a patient specific identification (i.e., a unique identifier associated with a particular patient). These objects are provided, according to the present invention, by providing file receptacles at locations within the medical facility where patient transfers take place such as outside examination rooms or at ancillary service stations. A patient's personal file is placed in the receptacles when a patient is brought to the location for a service. The receptacles include sensors which detect the presence of the file and which further detect and automatically acquire a patient identifier from the file. Both removal and insertion of files are detected which events are provided to a controller which time stamps the event for use in calculating information such as patient waiting time and examination time. Receptacles for files may be provided at various locations throughout the facility so that services provided to a patient along with the patient's location can be tracked throughout the course of the patient's visit to the medical clinic. A historical data base of patient wait times and treatment times, including patient specific tracking of such data, is also provided according to one embodiment of the present invention.

According to one embodiment of the present invention, a method is provided for automated patient tracking and data acquisition in a medical facility. A file having a patient identification indicator is associated with a patient entering the medical facility. Placement of the file in a first receptacle and a patient identification from the patient identification indicator is detected with a sensor associated with the first receptacle when the patient is moved to the first service location. Removal of the file from the first receptacle is then detected when a first service provider commences a service. Placement of the file in a second receptacle is detected upon completion of the service. The first and second receptacle may be the same receptacle. Alternatively, two separate receptacles may be utilized and the first may be associated with the physician and the second with a nurse. The receptacles in one embodiment of the present invention are located in the proximity of the service location. Where multiple service locations are provided in the medical facility, receptacles may be provided in the proximity of each service location where a patient may travel during a visit.

In a further aspect of the present invention, a patient visit data record may be generated corresponding to the patient visit. The generation of the patient visit data record may include determining the time between removal of the file from the first receptacle and placement of the file in the second receptacle to provide a treatment time and associating the determined treatment time with the patient visit data record. In a further aspect of the data acquisition aspects of the present invention, patient treatment times for additional services and patient wait times between services may also be determined, based on placement and removal of a patient file, and associated with the patient visit data record.

In another aspect of the present invention, an indication of patient status is provided to a first indicator associated with one of the receptacles based on placement of a file in one of the receptacles. An indication of patient status may also be transmitted to a second indicator located at a remote location from the service location. The indicator may be a light which may be turned on or off, or strobed, a buzzer or other audio indicator, or a display means capable of displaying text or graphical characters.

In a further embodiment of the methods of the present invention, a method is provided for automated patient tracking and data acquisition in a medical facility. Placement of a patient specific token in a first receptacle in the proximity of a first service location is detected with a sensor associated with the first receptacle when the patient is moved to the first service location. Removal of the patient specific token from the first receptacle is then detected when a first service provider commences a service. Placement of the patient specific token in a second receptacle in the proximity of the service location is then detected upon completion of the service. As services continue, removal of the file from the second receptacle is detected and placement of the patient file in a third receptacle in the proximity of a second service location with a sensor associated with the third receptacle is detected when the patient is moved to the second location. Removal of the file from the third receptacle is detected when a service provider commences a second service. Placement of the file in a fourth receptacle in the proximity of the second service location is detected upon completion of the service. The third and fourth receptacle may be the same receptacle or two separate receptacles.

While the present invention has been summarized above primarily with respect to the methods of the present invention, it is to be understood that the present invention is also directed to systems for carrying out the operations described above with respect to the methods aspects of the present invention as will be described more fully herein.

In one embodiment of the systems aspect of the present invention a system is provided for patient tracking and data acquisition. The system includes a first patient file receptacle configured so as to be mounted in the proximity of a patient service location. A patient identification indication reader is connected to the first receptacle and positioned so as to read a patient identification indication from a patient file positioned in the first patient file receptacle. Control means operatively connected to the patient identification reader and the file sensor generate patient visit data. In one embodiment of the systems aspect of the present invention, the system further includes a second patient file receptacle configured so as to be mounted in the proximity of a patient service location and a file sensor connected to the second receptacle and positioned so as to detect placement of a patient file in the second patient file receptacle.

The present invention overcomes the limitations of prior approaches to patient flow tracking in a medical clinic by providing a simplified means of automated patient tracking which requires, at most, minimal keyboard entry of information. The present invention further provides that the tracking may be patient specific based on detection of a patient identifier. Finally, the present invention provides for data acquisition of event activities from the automated patient tracking to generate patient visit data for subsequent analysis.

By providing a patient tracking and data acquisition system which automatically tracks patient location and status, provides communication between service providers, and marks events for time calculations, the present invention enhances physician and staff productivity, reduces waiting time, reduces or eliminates the need for paging or intercom messages and reinforces a standardized clinic process through an automated system based on receptacles for patient files which are typically used currently in medical clinics. In addition, tracking of time data and creation of a patient visit database provides a means for analysis of clinic processes, bench marking data, physician exam time data for comparison to billing codes and proactive customization of future patient scheduling and activity based costs and utilization data. The captured time data may also be used real time to provide the benefits of reduction in patient waiting time and increased waiting line fairness by prioritizing patient service access based on a fairness criteria linked to the patient's current visit service experience.

DETAILED DESCRIPTION OF ILLUSTRATED EMBODIMENTS

The present invention now will be described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

Figure 1:
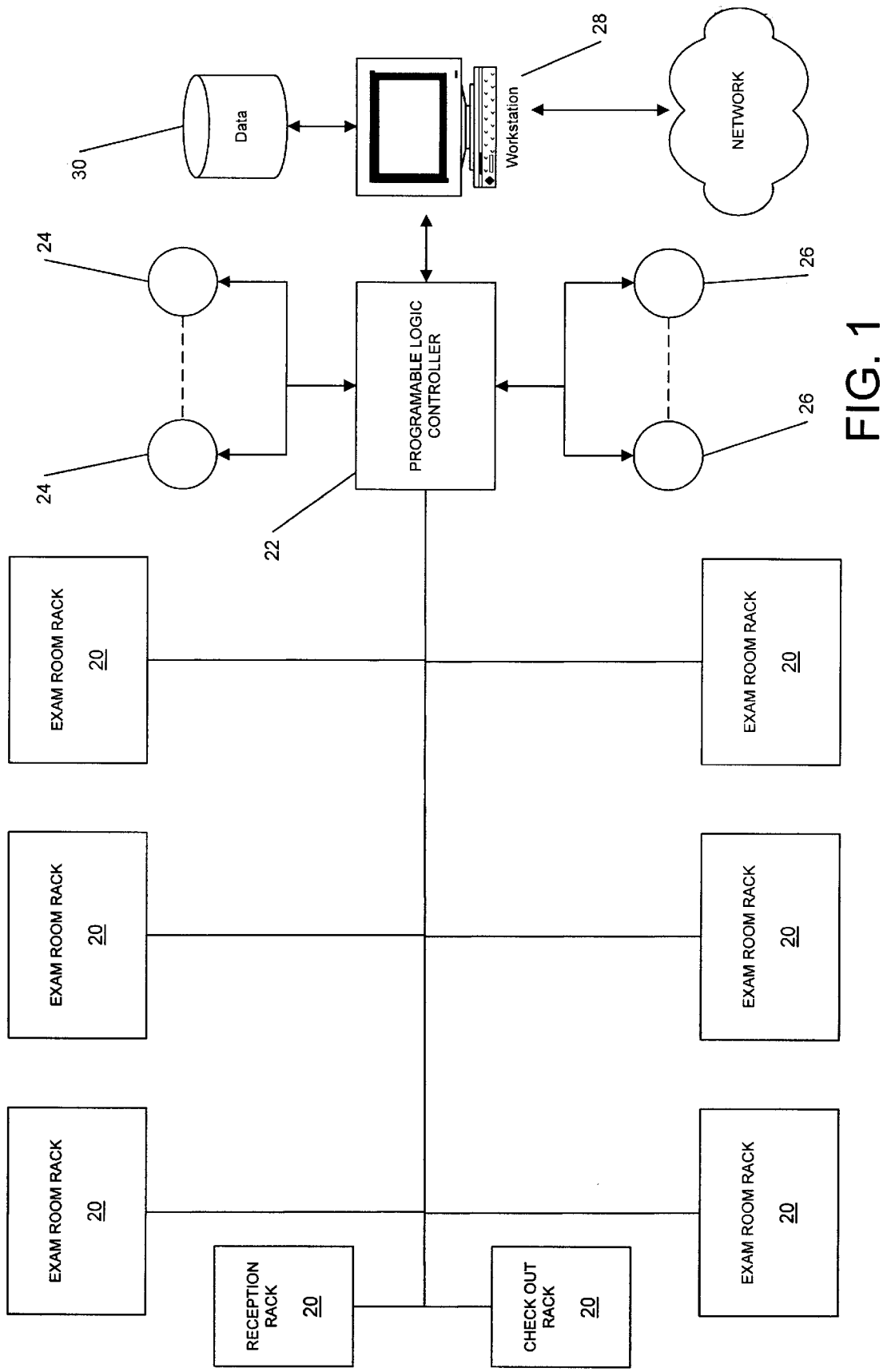
FIG. 1 is a block diagram illustrating the components of the system of the present invention according to an embodiment of the invention in an exemplary medical clinic environment.

Referring now to FIG. 1, an embodiment of a patient tracking and data acquisition system according to the present invention will now be described. FIG. 1 illustrates the components of an embodiment of the present invention in the context of a medical clinic. As shown in FIG. 1, a plurality of wall racks 20 containing file receptacles or other means for receiving and detecting a patient associated file are positioned at various locations within the medical clinic where patients are expected to be transferred between different service providers within the medical clinic. For example, as illustrated in FIG. 1, the medical clinic includes a plurality of exam rooms with a wall rack 20 provided at each exam room. Additional wall racks 20 are provided in the reception area and check out area. It is to be understood that the file receptacle need not take the form of a wall rack and may, for example, differ in structure between exam rooms and the reception or check out area where there is a potential for numerous patients to be queued at a single location concurrently.

As illustrated in FIG. 1, each of the wall racks 20 is operatively connected to programmable logic controller (PLC) 22 or other control means. PLC 22 is further operatively connected to and controls the operation of receptacle associated signal lights 24 or other indicating means and remote signal lights 26 or other indicating means. Receptacle signal lights 24 are preferably provided in wall racks 20 and are used to provide local displays of information on patient status as will be described further herein. Remote signal lights 26 are provided at other locations in the medical facility where indications of patient status or the location of service providers within the facility is desired. For example, a panel of remote signal lights 26 may be provided in a nurse's station, a breakroom or a physician's clinic. According to the present invention, receptacle signal lights 24 communicate status information related to patient services being provided at the local location of the wall rack 20. Remote signal lights 26 may be combined in a single location to provide information related to patient status and service provider activity in a plurality of locations throughout the clinic.

Also shown in the illustrated embodiment of FIG. 1 is computer 28 or other processing means. Computer 28 is operatively connected to PLC 22 and configured to receive data from PLC 22 related to detected patient tracking events. Computer 28 may also include means to transmit data to PLC 22, for example, to provide changes to the sequences algorithm associated with the PLC's 22 control of signal lights 24,26 responsive to file event and/or patient identification data collection from wall racks 20. Computer 28 is preferably a personal computer executing a data acquisition program for communicating with PLC 22 and for processing and storing data obtained from PLC 22.

According to the present invention, the data processing program of computer 28 analyzes events from patient file transfers during a patient visit to determine time and status information and generates a patient visit data record based on the services provided to a patient during a visit to the medical facility. Computer 28 is further operatively associated with database 30 so as to maintain a historical database of patient visit data records for subsequent analysis. While database 30, as illustrated, appears as a separate component from computer 28, it is to be understood that database 30 may be provided on a harddrive operatively associated and internally connected in computer 28. While not illustrated in FIG. 1, computer 28 may further be connected to a local area network having a plurality of additional computers interconnected over the network. In this manner, computer 28 interacting with database 30 may be accessed from various locations, such as individual physician's clinics, to draw upon historical patient visit data records for analysis and to check current status and location of patients.

Figure 2:
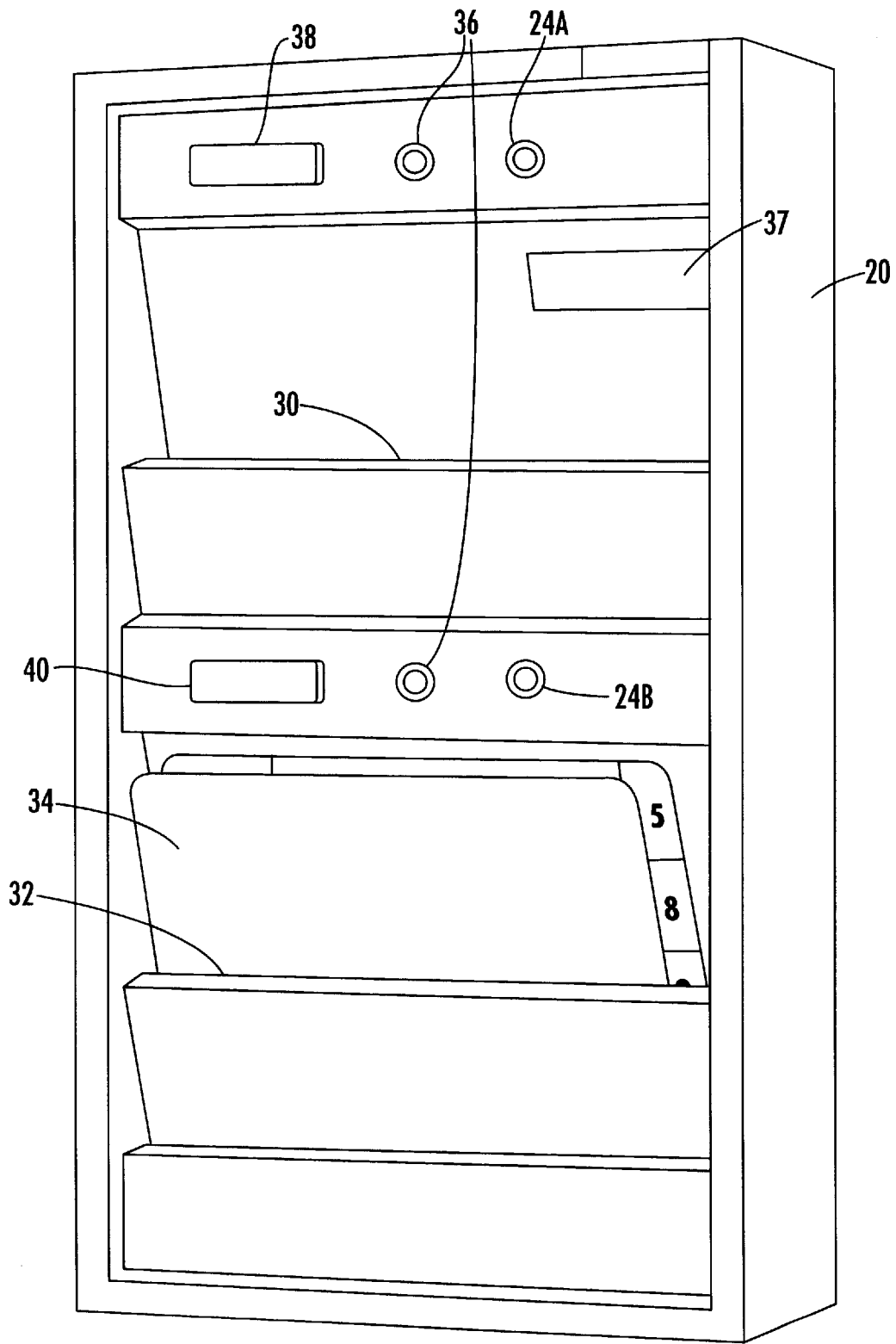
FIG. 2 is a perspective illustration of a wall rack according to an embodiment of the present invention.

Referring now to FIG. 2 a wall rack 20 according to an embodiment of the present invention will now be described. As illustrated in FIG. 2, a wall rack 20 includes two receptacles 30, 32. As shown in FIG. 2, second receptacle 32 includes a patient file 34 (sometimes referred to as a chart) placed within receptacle 32. Also illustrated in FIG. 2 are receptacle signal lights 24A and 24B associated with receptacles 30 and 32 respectively. Override switches (push buttons) 36 or other manual signaling means are also provided associated with each of receptacles 30 and 32. Also shown is scanner window 37. Service provider identifier labels 38, 40 are also shown. Identifiers 38 and 40 may be used to associate respective receptacles with particular service providers so as to provide a more reliable means for tracking the activities of individual service providers. For example, identifier 38 may list the name of a specific physician within the facility who has been assigned the examination room located in the proximity of wall rack 20. Identifier 40 may refer generally to a support personnel function such as a nurse, or alternatively, if specific rooms are assigned to individual nurses may designate the name of a specific nurse.

Figure 3:
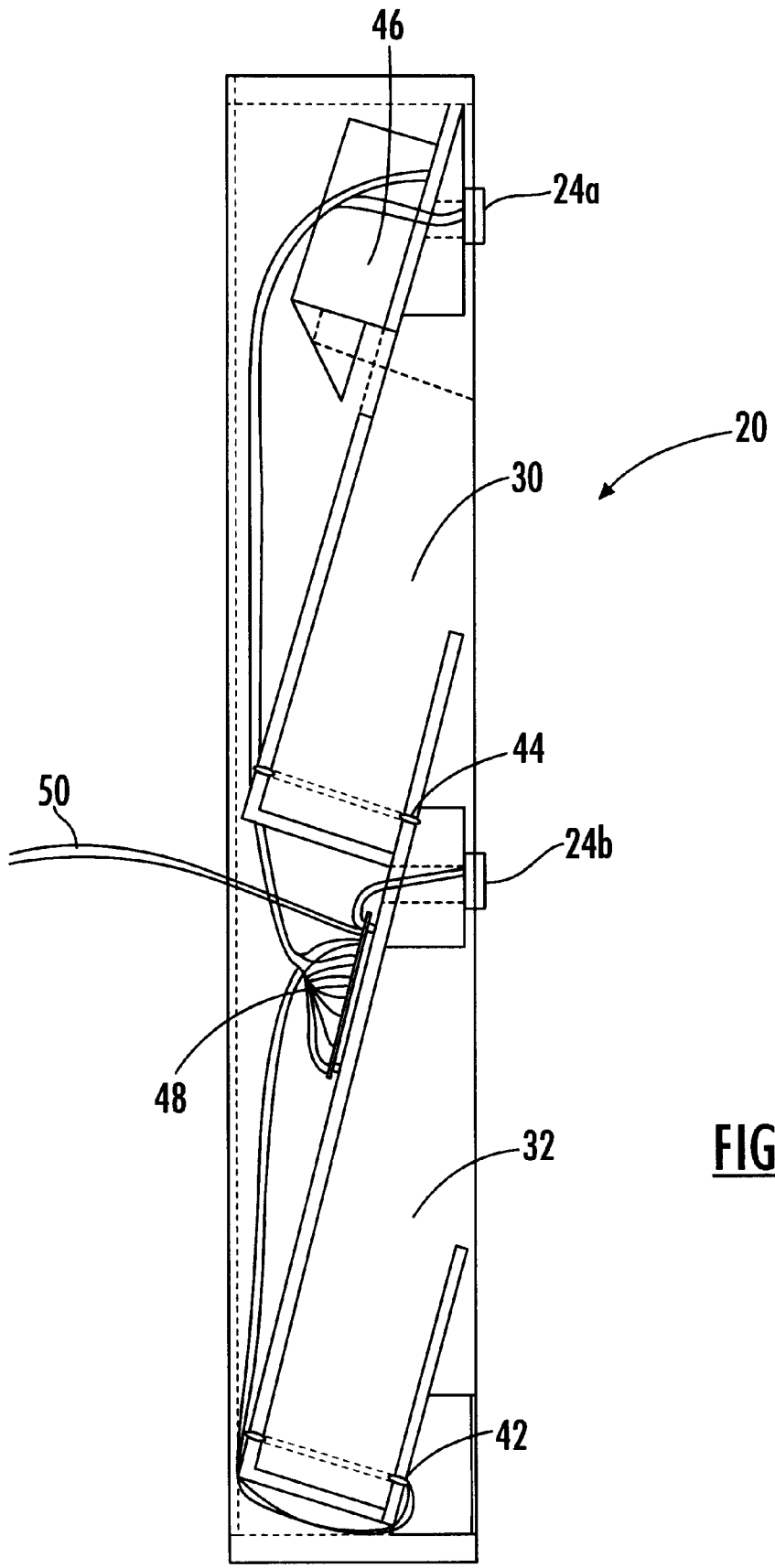
FIG. 3 is a cross-sectional view of the wall rack of FIG. 2 illustrating the sensor and indicator components of the wall rack.

Referring now to FIG. 3, the sensors and indicators provided in the illustrated embodiment of wall rack 20 in FIG. 2 will be further described with reference to a cross-sectional diagram showing the positioning and connection of the various sensor and indicators. Receptacle 32 includes infrared photodetector 42 or other sensor means positioned in a bottom portion thereof so as to detect placement or removal of a file 34 therefrom. Similarly, infrared photodetector 44 or other sensor means is provided so as to provide means for detecting placement of file 34 in receptacle 30. Also shown in FIG. 3, are indicator lights 24A and 24B. Patient identification information is read from file 34 by barcode scanner 46 or other patient identification indicator reading means.

As shown in the embodiment of FIG. 3, a single barcode scanner 46 is provided associated with receptacle 30 adjacent scanner window 37. However, it is to be understood that, alternatively, a second barcode scanner could be provided for reading identification information from a file 34 placed in receptacle 32. It is also to be understood that while a separate file placement detector 44 and barcode scanner 46 are shown in the embodiment of FIG. 3, barcode scanner 46 could be utilized for both detection of file placement/ removal and for reading patient identification.

Sensors 42, 44, and 46 are each operatively connected to printed circuit board (PCB) connector board 48 or other interface means. Indicator lights 24A and 24B also connect operatively to connector board 48. While not shown in FIG. 3, it is to be understood that override buttons 36 are operatively connected to connector board 48 as well. Connector board 48 provides means for connecting the sensors and indicators of wall rack 20 to PLC 22 by means of cable 50. While in the illustrated embodiment, the electrical connections of the sensors and indicators and switches to PLC 22 are by means of hard wires, it is to be understood that other means for operatively connecting the system components, such as wireless communication links, may be provided. For example, connector board 48 may include a radio transmitter and receiver for wireless communication with PLC 22. It is also to be understood that, while in the illustrated embodiment as shown in the figures, a separate PLC 22 and computer 28 are provided, the functions of both the PLC 22 and computer 28 may be provided by a single component of a computer rather than a separate logic controller interfaced to a computer.

Figure 4:
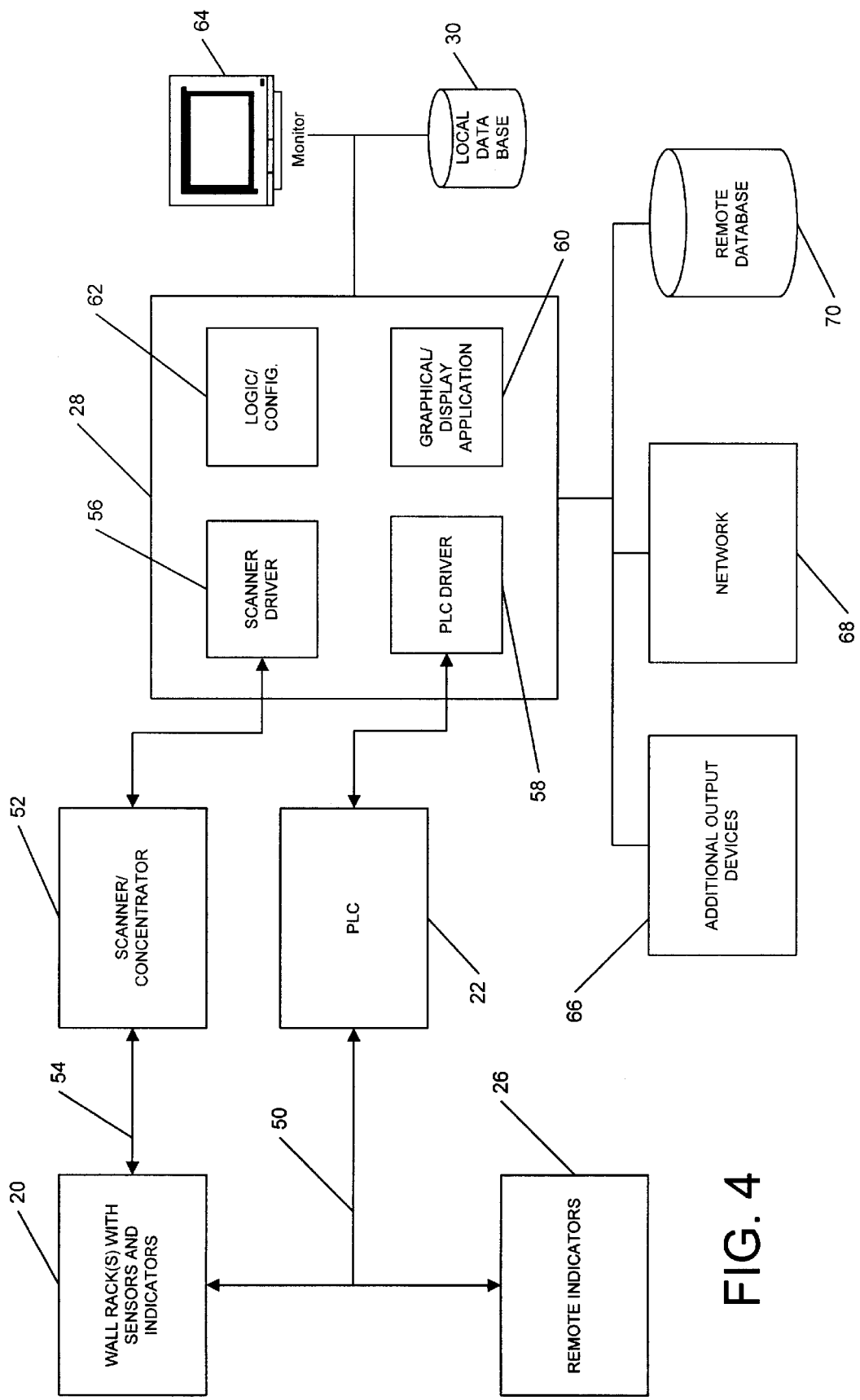
FIG. 4 is a block diagram illustrating a further embodiment of a system according to the present invention.

Referring now to FIG. 4, the operative interface between the components of the patient tracking and data acquisition system will be further described with reference to the block diagram illustration. Shown in FIG. 4 are PLC 22, computer 28 and database 30 which were discussed previously in connection with FIG. 1. Wall racks 20, including the various sensors and indicators as discussed in connection with FIGS. 2 and 3, are generally illustrated at block 20 of FIG. 4. The various remote signal lights are also illustrated at block 26. It is to be understood that indicators 24 and 26, while generally described herein as signal lights, may also take the form of audible tones or other means of indicating a status such as a character or graphics display means. As illustrated in FIG. 4, most of the sensors of wall rack 20 connect to PLC 22 over cable 50. However, barcode scanner 46, as shown in FIG. 4, is interfaced to scanner concentrator 52 over serial cable 54 rather than connecting through PLC 22. Remote indicators 26 are also operatively wired to PLC 22.

The various functions of computer 28 are shown in further detail in FIG. 4. Scanner driver interface 56 is operatively connected to scanner concentrator 52 to process incoming scanned information. Alternatively, scanner 46 may directly connect to PLC 22 or computer 28. PLC driver 58 is operatively connected to PLC 20 to provide communications between PLC 22 and computer 28. Logic/configuration application 62 provides an interface to scanner driver 56, PLC driver 58, graphic/display software 60, local database 30 (associated with computer 28) and remote database 70. Monitor 64 or other display means provides a display means for computer 28.

Further illustrated in FIG. 4 are various additional devices which may be accessed by computer 28 through provision of appropriate interface software applications on computer 28 and required hardware connections. These additional features include various additional forms of output indicators such as text displays, for example, message board displays, such as pagers or phones indicated generally in FIG. 4 at block 66. As discussed previously, computer 28 may be connected over a local computer network operating a protocol such as TCP/IP or other protocol which network is generally illustrated in FIG. 4 at block 68. Access to additional storage means containing other databases may also be provided to computer 28 as illustrated at block 70. In practice, additional databases 70 may physically be stored on a common harddrive associated with computer 28 and containing database 30. Additional databases 70 may also be associated with other computers on network 68 in which case computer 28 would access such databases over network 68.

While the description above has been directed to an embodiment of the present invention where the patient identification token is a patient file 34, such as those typically encountered in a medical clinic, with the addition of a barcode label or other patient identification indicator affixed to a back face thereof so as to be placed adjacent barcode scanner 46 when a file 34 is placed in receptacle 30, other approaches are also to be understood as within the scope of the present invention. For example, different means of automated patient identification may be utilized in place of a barcode. Examples of alternative approaches which may be used with the present invention include magnetic ink character recognition, optical character recognition and magnetic stripe. Furthermore, while in the illustrated embodiment it is envisioned that a simple printed label or other indicator may be affixed to the back of a normal patient file folder, it is also to be understood that it is anticipated within the scope of the present invention that a card type component may be attached to or associated with the file and placed in a card reader at the time the file is placed in wall rack 20.

It is also possible to utilize a patient tracking token rather than a file in accordance with the present invention. For example, an electronic token may be utilized containing the patient information in place of or in addition to a file. However, in the preferred embodiments of the present invention, in which the benefits of the present invention may be best realized in a reliable manner consistent with existing practices within a medical facility, the patient tracking token takes the form of an object such as the patient file 34 which is already in use and moves with the patient throughout the facility. Utilization of a token separate from the file would present an added disadvantage in imposing on the service provider employees an additional step or operational requirement to support the data entry for patient tracking. Doing so would increase the potential for errors or oversights in patient tracking and data acquisition based upon oversights by personnel.

Furthermore, it is to be understood that, while not in widespread use, known technologies are currently available, such as smart cards, which would serve as electronic patient files and may, in the future, provide the same function and move with a patient in the same manner as paper files. For purposes of the present invention, the term "file" is intended to encompass a patient file whether in a paper or electronic form depending upon the format used for a patient file in the medical clinic and which would move along with a patient during a visit to the medical clinic.

As will be appreciated by those of skill in the art, the above described aspects of the present invention in FIGS. 1, and 4 may be provided by hardware, software, or a combination of the above. While the various components of the systems of the present invention have been illustrated in part as discrete elements in these figures, they may, in practice, be implemented by a microcontroller including input and output ports and running software code, by custom or hybrid chips, by discrete components or by a combination of the above.

Operations of the Present Invention for Automated Patient Tracking

Operations according to various embodiments of the present invention will now be described more fully with reference to the flowcharts contained in FIGS. 5–8. As an aid to understanding the operations of the present invention, an exemplary patient experience in a physician's facility will first be described to provide a context for a description of operations of the present invention.

In a medical facility, a patient typically goes through a multiple step process where the patient checks in, and moves from the care of one service provider to another as the patient moves from one location to another. Within medical ambulatory treatment facilities a standard process or procedure for handling a patient is typically provided which patients generally follow from check in through check out. While there may be variations expected in the specifics of services provided to particular patients, various of the steps, such as check in, check out and treatment by a nurse and a doctor, are typically experienced in almost all cases. During the processing, a patient file is generally moved by the service providers along with the patient as the file is used by the physician as a repository of treatment information related to the patient both from a current visit and reflecting historical treatments so that this information will be available to the nurse and/or doctor during an examination of the patient. The file may also be used for tracking billing and payment. For example, a treatment form is typically provided with the file as it moves with the patient on which each service provider checks off, for example, boxes to indicate the specific services provided. On check out, the accounting personnel of the service provider review the checked boxes to identify the services provided and then access the database advising them of the rate for the specific services so a total charge to the patient may be determined at the end of the visit.

While the patient's chronological experience of a visit to a medical facility will now be described with respect to a single patient, it is to be understood that, from the perspective of the service provider, a plurality of patients are being treated at any one time so that each service provider is, preferably, able to perform appropriate services throughout the course of the work day as various patients are processed. In addition, it is to be understood that, typically, a plurality of patients are being processed through a clinic visit concurrently for each service provider. For example, a single physician may have three associated examination rooms allowing up to three patients to be in place and ready for examination by the physician at any point in time.

An exemplary patient visit experience may include the following steps from entry of the patient to the facility to exit of the patient: 1) check in (wait for nurse triage); 2) nurse triage; 3) wait for physician; 4) physician exam; 5) wait for nurse; 6) nurse procedure or final instructions; 7) in transit to check out; 8) check out. Note that, for purposes of simplifying the explanation, no ancillary services, such as collection of samples or lab testing, are separately illustrated at ancillary lab locations (either within the clinic or at a separate location). The patient's access to these ancillary services may be based on samples taken during the nurse or physician examination or treatment periods described above and the patient need never move to the ancillary location for the laboratory services. However, it is to be understood that if the alternative approach of designating required tests and sending the patient to a separate ancillary service provider for collection of samples for testing is used, according to the methods of the present invention, patient tracking in movement to the lab location will also be included in the above process.

Each of the steps in the patient process described above typically requires a transfer from one service provider to another and may involve physical movement of a patient between various locations, such as from the reception area to the exam room in step 2 and from the exam room to the check out desk in step 7. Mismanagement of patient transfers may result in inconsistent treatment of patients. Furthermore, communication among providers, such as nurses and physicians, may be accomplished through disruptive pages or intercom messages or through personal contact after utilizing resources to search for the provider to be provided information. For example, nurses may walk up to a reception area simply to see if any new patients have arrived if they are not provided with a reliable means for prompting them that patients are waiting. In addition to lacking a means for patient flow tracking and notification, current physician office practices typically perform no time data tracking due to difficulty in cost of collecting such information.

Figure 5:
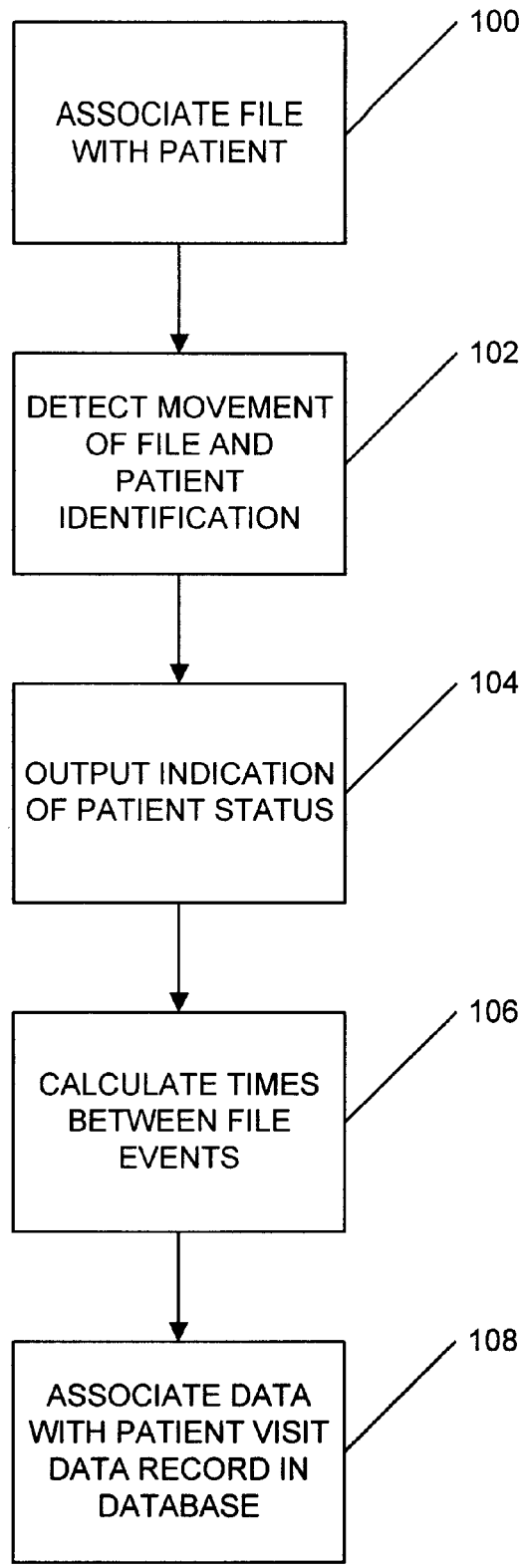
FIG. 5 is a flowchart illustrating operations according to an embodiment of the present invention.

Referring now to FIG. 5, operations according to an embodiment of the present invention for patient tracking and data acquisition in a medical clinic will now be described. At block 100, a file 34 having a patient identification indicator, such as barcode label affixed to an external surface, is associated with a patient entering the medical facility. For a new patient, this may involve obtaining a new blank file, setting up the appropriate internal tracking documents for maintaining a medical history and payment records and affixing a patient identifier which may be the patient's name, but is often a numerical designation associated with a particular patient for data tracking within the medical facility. According to the present invention, a barcode label is also preferably attached to the back of the file which provides a patient identification indicator to the file which may be read by barcode scanner 46. For a returning patient, these steps are generally unnecessary and an existing file is pulled, for example, from a file room, and a treatment sheet may be added on which the various service providers will make notations of the services provided as the patient progresses through the visit.

Movement of the file is tracked according to the present invention for the balance of the time the patient is in the medical facility through checkout as illustrated at block 102. Tracking of the patient may actually commence in the receiving area by placing the file in a receptacle, with appropriate sensors, on entry of the patient to the facility. Alternatively, tracking may not commence until a patient is moved to an exam room and the file is placed in the nurse associated receptacle 32 of wall rack 20. It is to be understood that placement of detection type receptacles at greater numbers of locations provides the ability for increased detail in tracking of patient movement with greater "granularity" in details of the resulting acquired data characterizing the patient's experience but is provided at the cost of additional hardware requirements.

Assuming placement of a receptacle in the reception area, tracking starts when the file is placed in the reception area receptacle. This corresponds to a start time event for check in item 1 of the exemplary process listed above. In addition to detecting placement of the file in the first receptacle, a patient identification is detected or read from the patient identification indicator with sensor 46 associated with the first receptacle when the patient arrives at the location where the first receptacle is located. Accordingly, with the illustrated embodiment of the wall rack 20 in FIG. 3, the initial file 34 placement will be in receptacle 30 which includes barcode scanner 46.

Removal of file 34 from the first receptacle is then detected and marked as an event indication associated with the event of commencement of service by the first service provider. For example, removal of the file from the first receptacle 30 would indicate the end of the check in wait period and commencement of the nurse triage step above. Upon completion of the nurse triage, the file is placed back in wall rack 20, for example, in receptacle 30 to indicate the patient is ready for physician examination. The detected placement of file 34 in the receptacle upon completion of nurse triage provides an event timer marker ending the period for nurse triage and beginning the wait time calculation for physician treatment.

This process of detecting placement and removal of the file in receptacles continues through each step of processing until check out. It is also to be understood that multiple receptacles are not required in wall rack 20 to obtain the benefits of the present invention. However, use of multiple receptacles within wall rack 20 provides the ability for more detailed tracking of patient treatments by providing a means to associate respective receptacles with different service providers. So long as a consistent sequence of operations is provided in placement of files, however, the logic programming of PLC 22 may provide a means associating each event with an appropriate step in the process to create accurate event markers for subsequent time analysis and further for use in determining what indications are required to be provided on indicators 24, 26.

Patient status output indications are further provided according to the present invention as indicated at block 104 of FIG. 5. Indications may be provided reflecting the status of a patient or what service is currently required for that patient. The logic of controller 22 may further provide sequencing control for providing indications of priority of service to the various providers. For example, the physician receptacle associated indicator light 24A (in FIG. 2) may be turned on continuous to indicate the presence of a patient in the exam room associated with rack 20. When it is determined that the patient in the exam room associated with rack 20 is the next patient requiring service, indicator 24A may be driven in a blinking manner. Further variations on the use of an indicator light may include changing the blink rate to create a strobe effect as an indication that the physician is currently in the exam room and treating the patient. Alternative logical sequences of using a single signal light to communicate multiple states are to be understood to be within the scope of skill of one of ordinary skill in the art and will not be discussed further herein. Similar indications of patient status may be provided at remote locations using indicators 26.

In addition to providing indications of the state of service and location for each patient, separate remote display panels may be provided structured to reflect and track the current location of the service providers such as the physicians. For example, a specific physician may have three exam rooms assigned for patient exams by that physician during the course of a day. As the present invention allows automated tracking of when a physician is in an exam room performing an examination, the remote indicators 26 may be grouped in sets corresponding to exam rooms associated with a particular physician to provide indication of where that specific physician is when the physician is in one of the three assigned exam rooms. The three indicator lights may then be provided at a remote location such as a nurse station with a light turned on reflecting the exam room the physician is presently in, thereby facilitating locating the physician for delivery of messages during the course of the day. Similar tracking may be provided for support personnel such as nurses.

In addition to providing automated patient tracking of patient location and status, the present invention further provides for automated data acquisition related to patient treatment experiences. A patient visit data record may be generated to capture the treatment experience for a patient during a visit. Accordingly, at block 106, computer 28, based upon event information provided by PLC 22, calculates the times between various file events. Based upon the various event time of occurrences and knowledge of patient operations, computer 28 is able to recreate the time duration of each of the steps described for the exemplary patient experience described above including waiting times, such as check-in, wait for the physician and wait for a nurse, as well as treatment times such as nurse triage, physician exam and nurse final instruction procedures and total visit time. As illustrated at block 108, this patient data is associated with a specific patient visit data record. In embodiments of the present invention where patient identification is automatically acquired, the patient visit data record is associated with the patient identification for that patient. Alternatively, keyboard entry may be used to provide patient specific association of each patient visit data record generated by the methods of the present invention. In a simplified embodiment of the present invention, patient visit data records are collected without an associated patient specific identifier to obtain aggregate treatment rather than patient specific treatment experience data. In addition, in creating the patient visit data record at block 108, the patient visit data records are stored in database 30.

Figure 6:
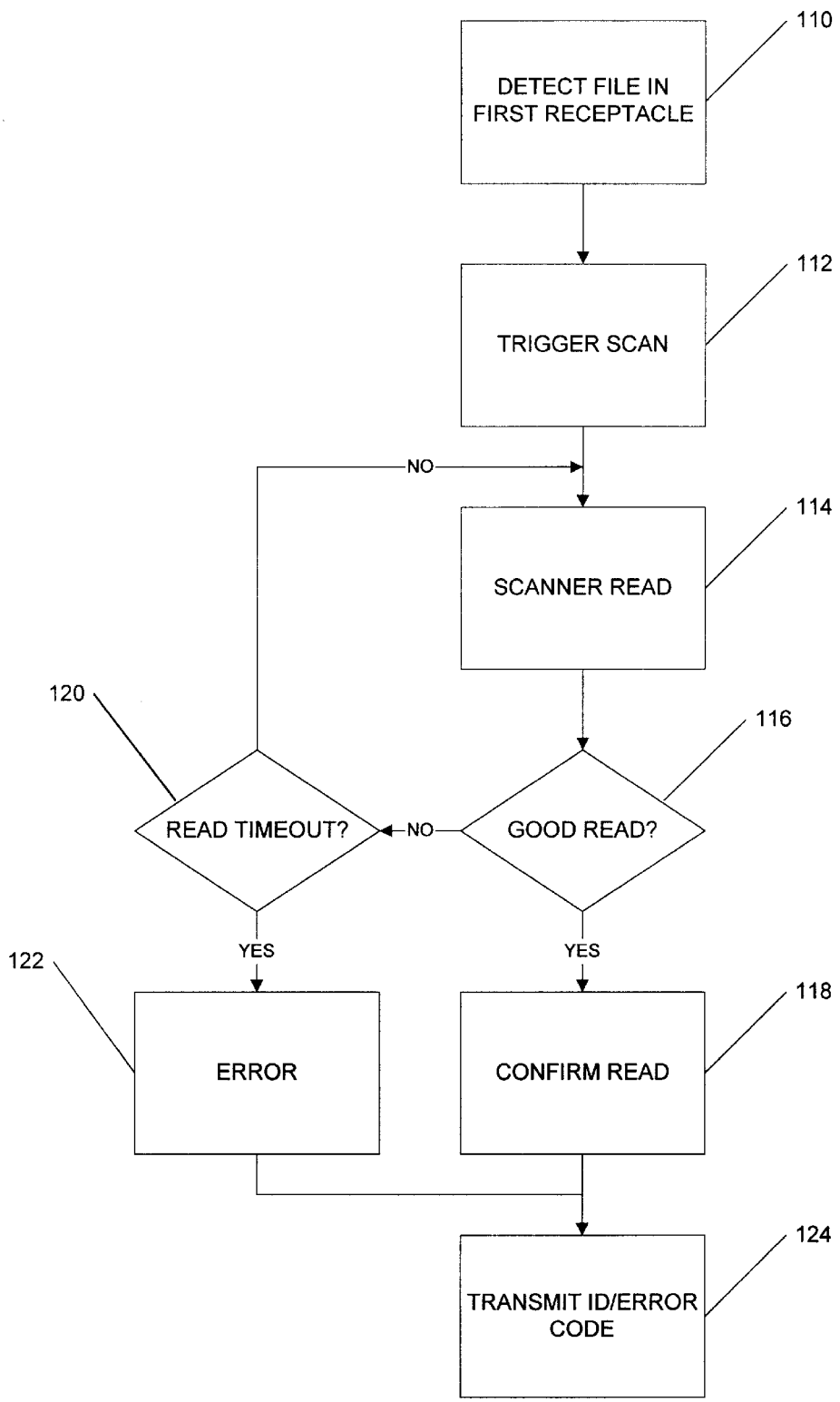
FIG. 6 is a flowchart illustrating operations for patient identification scanning according to an embodiment of the present invention.

Operations according to the present invention will now be further described with reference to the flowcharts of FIGS. 6–8. Referring first to FIG. 6 at block 110, a chart is placed in first receptacle 30 of wall rack 20. Infrared photodetector switch 44 in receptacle 30 then triggers a read by scanner 46 at block 112. Placement of the chart at block 110 also triggers operations by PLC 22 in turning on appropriate indicator lights 24,26. At block 114, scanner read cycle operations take place to obtain patient identification information. If a successful read is detected at block 116, an indication of successful read such as, for example, a beep is provided at block 118. If a successful read is not detected at block 116, the read cycle timeout is checked at block 120. If the maximum allowed time for attempting to read identification information has passed at block 120, operations proceed to block 122 and a read error message is generated to indicate a failure condition. Otherwise, operations move from block 120 to block 114 to continue to attempt to obtain a good reading with scanner 46. At block 124, the scan signal from detector 46 is transmitted, for example, through scanner concentrator 52 to computer 28.

Figure 7:
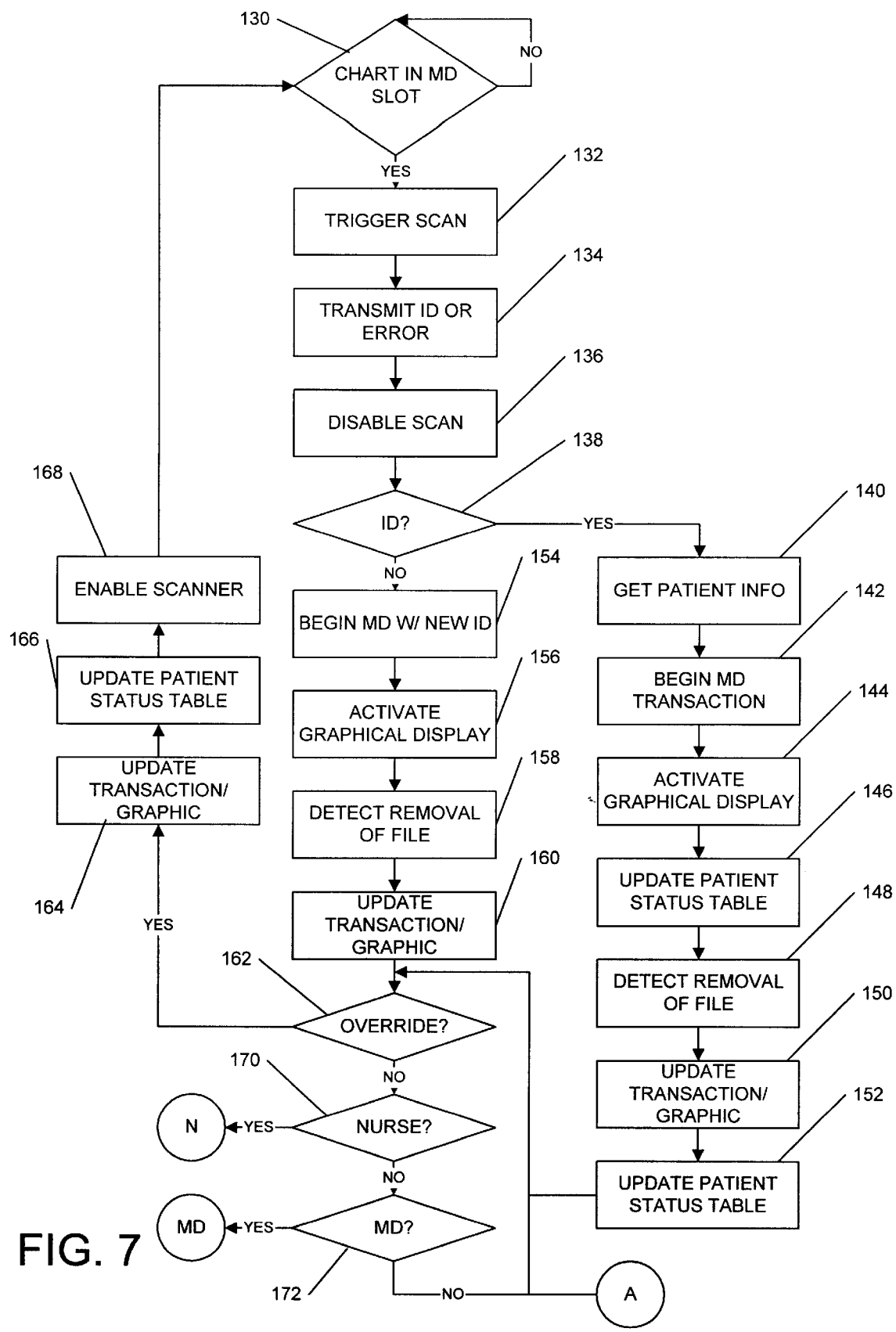
FIG. 7 is a flowchart illustrating operations for data acquisition and patient tracking according to an embodiment of the present invention.

Referring now to FIG. 7, operations related to creating patient visit data records will be further described for a particular embodiment of the present invention. When placement of a file 34 in physician receptacle 30 is detected at block 130, triggering of infrared switch 44 also triggers the scanner read at block 132 as described above with respect to FIG. 6. Computer 28 receives a scanned ID or an error message from the scanner at block 134. At block 136, scanner operations are disabled, preferably by setting a control bit to a disable state. If a successful patient identification was read, operations at block 138 move to block 140 and a patient data table, for example, in database 30, is checked for a name and/or other stored data associated with the scanned patient identifier. A physician examination transaction with the associated ID is then generated at block 142. At block 144, a graphical display, such as a display representing the medical clinic layout, is initiated to indicate room status on display 64. A graphical display may include the identification of a patient and/or provider in a room, the visit type, the status of the patient and the status of the room. At block 146, a patient status screen (table) is updated for monitor 64 to indicate a physician is being waited on in the associated examination room number. The patient status screen may include the patient name, visit type, scheduled physician, appointment time, total face-to-face time and recommended CPT code. At block 148, removal of the file 34 from the physician slot 30 is detected. Subsequently, at block 150, the physician examination transaction is updated to indicate the end of the wait time along with the graphical display. The patient status screen is then updated to indicate a physician is in exam room and the associated room number at block 152. A user may select between the graphical display or the patient status screen for viewing on monitor 64 or multiple monitors or windows on a single monitor may be used to display both screens.

Operations proceed somewhat differently if the scanner was unable to successfully read a patient ID as determined at block 138. In this case, operations proceed to block 154 and the physician examination transaction is created with the unique ID generated by computer 28. At block 156 the graphical display is initiated. At block 158, removal of the file from the receptacle is detected and the physician examination transaction is updated to indicate the end of the wait time. At block 160, the graphical display is updated to reflect a physician examination is in process in the exam room. Operations then proceed from either block 160 or block 152 to block 162 to determine if the examination room available indication has been received. According to the illustrated embodiment of the present invention, availability of the examination room is indicated to the computer 28 after all of the patient treatment steps associated with that service location are completed for that visit. This is done by the last service provider pressing override button 36.

If processing of a particular patient through that examination room is indicated at block 162, an exam end time is added to the transaction at block 164 and the graphical display is updated to indicate that the room is available. At block 166, the patient status screen will then be updated to show that the patient is in transit to a new location and this information may be displayed on display 64.

At block 168, the scanner 46 for wall rack 20 is re-enabled by resetting the disabled bit. By disabling scanner operations at block 136 and re-enabling operations at block 168, repeated transfers of a specific patient between a first and second service provider such as a physician and a nurse during a single visit to a specific examination room may be processed without the requirement of initiating a new scan to identify a change in patient identification. Use of the override button 36 to close out transactions further allows a determination of an end of an examination time period without including the overhead time during which the patient is in transit to another location within the medical facility, thereby providing a more accurate tracking of the duration of various examinations.

If the room available indication has not been received from override button 36 at block 162, operations proceed to block 170 to determine if file 34 has been detected as being placed in second (or nurse's) slot 32. If so, operations continue as will be described with respect to FIG. 8. If the file 34 has not been placed in nurse slot 32, operations proceed to block 172 to determine if the file 34 has been placed in physician slot 32 at block 172. If so, operations continue as will be described with respect to FIG. 9.

Figure 8:
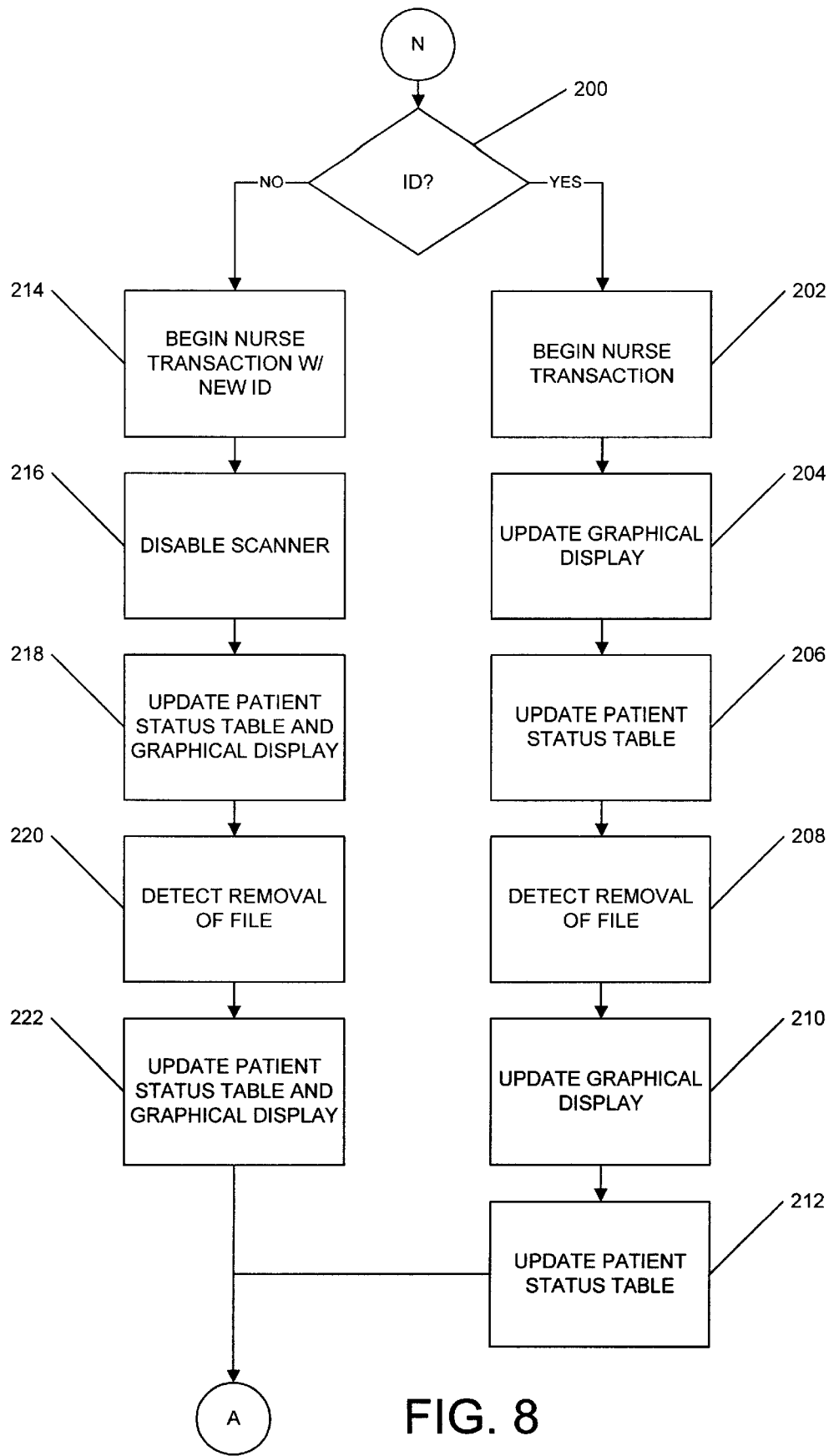
FIG. 8 is a flowchart illustrating further aspects of operations for data acquisition and patient tracking according to the embodiment of the present invention of FIG. 7.

Referring now to FIG. 8, when a placement of file 34 in nurse receptacle 32 has been detected (block 170 of FIG. 7), operations proceed to block 200 to determine whether a patient ID or a system generated unique identifier has been generated for the file. If so, operations proceed to block 202 and computer 28 initiates a nurse procedure transaction associated with the available ID. At block 204 the graphical display is updated. At block 206, the patient status screen (table) is updated to indicate the nurse wait condition and the associated examination room number for the patient. At block 208, removal of file 34 from nurse receptacle 32 is detected. The graphical display is then updated at block 210. At block 212, the patient status screen is updated to reflect the nurse procedure underway condition and the associated room number for the patient.

If no patient ID or unique identifier number is detected as available at block 200, such as would occur when using the embodiment of the wall rack 20 of the present invention illustrated in FIGS. 2 and 3, where only a single scanner is included and the file was placed first in nurse receptacle 32 where no scanner 46 was present, the nurse procedure begins at block 214 by establishing a new ID at computer 28 to associate with the procedure. At block 216, scanner operation is disabled similarly to the operations previously described in connection with FIG. 7, block 136. At block 218, the graphical display is updated to reflect a wait for nurse condition (as is the patient status screen (table). Removal of file 34 from nurse receptacle 32 is detected at block 220 after which operations at block 222 update the graphical display to indicate initiation of nurse procedures. Operations continue after block 212 or block 222 by returning to the wait loop as indicated by off-page connector A and checking for placement of file 34 in receptacle 30 or receptacle 32.

Figure 9:
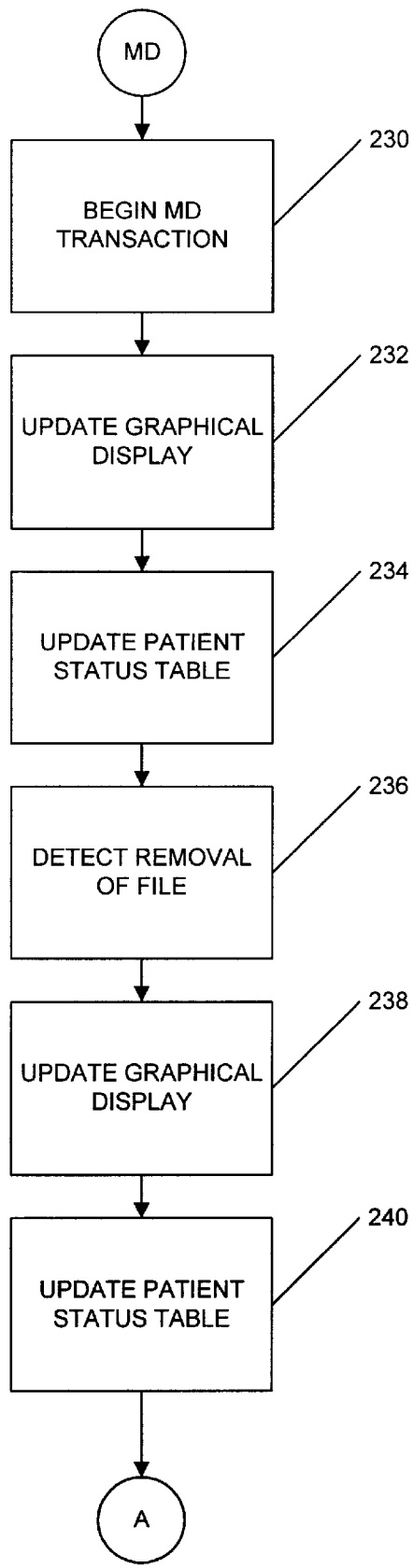
FIG. 9 is a flowchart illustrating further aspects of operations for data acquisition and patient tracking according to the embodiment of the present invention of FIG. 7.

Operations following detection of placement of a file 34 in a physician slot 30 at block 172 of FIG. 7 begin at block 230 of FIG. 9 by starting a physician examination transaction with the already established identification number. At block 232 the graphical display is updated with an indication of waiting for physician treatment condition. The patient status screen (table) is updated at block 234 to indicate the waiting for physician treatment condition and the room number associated with the patient. Removal of file 34 from receptacle 30 is subsequently detected at block 236. At block 238 the graphical display is updated to indicate physician examination underway condition and the patient status screen (table) is updated at block 240 to indicate a physician examination is underway and the associated room number for the patient. Operations after block 240 return to the wait loop for detecting file placement as indicated by the off-page connector A referring to FIG. 7.

As will be understood from the description from the systems and methods of the present invention above, a variety of data acquisition information is provided according to the present invention. Time data points or patient procedures as illustrated above which are captured by the system include check in; begin waiting in the reception; end waiting in the reception; begin triage process; end triage process; begin wait for physician; end wait for physician; begin physician exam; end physician exam; begin wait for nurse; end wait for nurse; begin nurse procedure; end nurse procedure; begin transit; check out; begin wait for ancillary service; end wait for ancillary service; begin ancillary service; end ancillary service and so on depending upon how many subsequent sequential steps the patient's visit proceeds through. It will also be understood that the order of these different operations may change in any particular embodiment. In addition to the event time marks as described, the system may further provide patient counts and room usage.

From the data automatically acquired according to the present invention, it is to be understood that various relevant information related to patient visit performance may be determined by computer 28. Examples of such information include calculations of total visit time; recommended billing codes; waiting room time; triage time; wait for physician time; physician examination time; wait for nurse time; nurse procedure time; transit time; wait for ancillary service time; ancillary service time; room utilization; room turnover rate; on time arrival; walk in rates and so on as will be understood by medical clinic service providers to assist in analysis and optimization of service delivery by such providers.

The present invention provides various capabilities in its various embodiments including automated acquisition of event information, patient and provider specific data tracking, time and sequence tracking of patient flow, communication of status information to providers, capacity for programmatic control over priority and waiting time for a plurality of patients being concurrently processed in a medical facility, and off line access to historical performance data based on patient visit data records.

The present invention has been described above with respect to FIGS. 5 through 9 with reference to flowcharts illustrating the operation of the present invention. It will be understood that each block of the flowchart illustrations, and combinations of blocks in the flowchart illustrations, can be implemented by computer program instructions. These program instructions may be provided to a processor to produce a machine, such that the instructions which execute on the processor create means for implementing the functions specified in the flowchart block or blocks. The computer program instructions may be executed by a processor to cause a series of operational steps to be performed by the processor to produce a computer implemented process such that the instructions which execute on the processor provide steps for implementing the functions specified in the flowchart block or blocks.

Accordingly, blocks of the flowchart illustrations support combinations of means for performing the specified functions, combinations of steps for performing the specified functions and program instruction means for performing the specified functions. It will also be understood that each block of the flowchart illustration, and combinations of blocks in the flowchart illustration, can be implemented by special purpose hardware-based systems which perform the specified functions or steps, or combinations of special purpose hardware and computer instructions.

In the drawings and specification, there have been disclosed typical preferred embodiments of the invention and, although specific terms are employed, they are used in a generic and descriptive sense only and not for purposes of limitation, the scope of the invention being set forth in the following claims.

That which is claimed is:

1. A method for automated patient tracking and data acquisition in a medical facility comprising the steps of:
    providing a file folder having a patient identification indicator mounted thereon;
    associating the file folder and the patient identification indicator with a patient entering the medical facility;
    automatically detecting placement of the file folder in a first receptacle and a patient identification from the patient identification indicator with a sensor associated with the first receptacle when the patient is moved to the first service location;
    automatically detecting removal of the file folder from the first receptacle when a first service provider commences a service; and
    automatically detecting placement of the file folder in a second receptacle upon completion of the service.

2. A method according to claim 1 wherein said first receptacle and said second receptacle are the same receptacle.

3. A method according to claim 1 wherein said first receptacle is a physician receptacle and said second receptacle is a nurse receptacle.

4. A method according to claim 1 further comprising the step following said step of associating the file folder and the patient identification indicator with a patient entering the medical facility of generating a patient visit data record.

5. A method according to claim 4 wherein said step of generating a patient visit data record includes the steps of:
    determining the time between removal of the file folder from the first receptacle and placement of the file folder in the second receptacle to provide a treatment time; and
    associating the determined treatment time with the patient visit data record.

6. A method according to claim 1 wherein the first receptacle and the second receptacle are located in the proximity of the first service location and further comprising the step of:
    providing an indication of patient status to a first indicator associated with one of the first receptacle or the second receptacle based on placement of the file folder in at least one of the first receptacle or the second receptacle.

7. A method according to claim 6 further comprising the step of:
    transmitting an indication of patient status to a second indicator located remotely from the first service location.

8. A patient tracking and data acquisition system comprising:
    a first patient file receptacle configured so as to be mounted in the proximity of a patient service location;
    a patient identification indication reader connected to the first receptacle and positioned so as to read a patient identification indication mounted on a patient file folder positioned in the first patient file receptacle; and control means operatively connected to said patient identification reader and said file sensor for generating patient visit data.

9. A system according to claim 8 further comprising:

a second patient file receptacle configured so as to be mounted in the proximity of a patient service location; and a file sensor connected to the second receptacle and positioned so as to detect placement of a patient file folder in the second patient file receptacle.

10. The system according to claim 8 further comprising:

a file sensor connected to the first receptacle and positioned so as to detect placement of the patient file folder in the first patient file receptacle, wherein the system operates the patient identification indication reader to read the patient identification indication mounted on a patient file folder responsive to detection of the patient file folder by the file sensor.

11. A method for automated patient tracking and data acquisition in a medical facility comprising the steps of:

providing a file folder having an electronically readable patient identification indicator mounted thereon;

associating the file folder and the patient identification indicator with a patient entering the medical facility such that the patient identification indicator includes a patient identification that uniquely identifies the patient;

automatically detecting placement of the file folder in a first receptacle and the patient identification from the patient identification indicator with a sensor associated with the first receptacle when the patient is moved to a first service location;.

automatically detecting removal of the file folder from the first receptacle when a first service provider commences a service; and automatically detecting placement of the file folder in a second receptacle upon completion of the service.

12. The method of claim 11 wherein said step of automatically detecting placement of the file folder in a first receptacle and the patient identification from the patient identification indicator includes:

detecting the placement of the file folder in the first receptacle using a file sensor; and responsive to the detection of the file folder by the file sensor, actuating a patient identification indication reader to read the patient identification from the patient identification indicator.

* * * * *